(12) United States Patent
Gutwein et al.

(10) Patent No.: US 10,888,348 B2
(45) Date of Patent: Jan. 12, 2021

(54) DEVICE AND METHOD FOR SCAR SUBCISION

(71) Applicant: Indiana University Research and Technology Corporation, Indianapolis, IN (US)

(72) Inventors: Luke G. Gutwein, Franceville, IN (US); Rajiv Sood, Carmel, IN (US); Barry Davignon, Terre Haute, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/783,559

(22) Filed: Feb. 6, 2020

(65) Prior Publication Data
US 2020/0170658 A1   Jun. 4, 2020

Related U.S. Application Data

(63) Continuation of application No. 15/745,955, filed as application No. PCT/US2016/046345 on Aug. 10, 2016.
(Continued)

(51) Int. Cl.
*A61B 17/3201* (2006.01)
*A61B 17/285* (2006.01)
(Continued)

(52) U.S. Cl.
CPC ........ *A61B 17/3201* (2013.01); *A61B 17/285* (2013.01); *A61B 2017/00353* (2013.01);
(Continued)

(58) Field of Classification Search
CPC .............. A61B 17/285; A61B 17/3201; A61B 2017/00353; A61B 2017/00792;
(Continued)

(56) References Cited

U.S. PATENT DOCUMENTS

| 4,285,344 A | 8/1981 | Marshall |
| 5,478,347 A | 12/1995 | Aranyi |

(Continued)

FOREIGN PATENT DOCUMENTS

| CN | 201617909 | 11/2010 |
| CN | 202154724 | 3/2012 |

(Continued)

OTHER PUBLICATIONS

International Search Report and Written Opinion issued by the European Patent Office, dated Nov. 2, 2016, for International Patent Application No. PCT/US2016/046345; 10 pages.
(Continued)

*Primary Examiner* — Shaun L David
*Assistant Examiner* — Christina C Lauer
(74) *Attorney, Agent, or Firm* — Faegre Drinker Biddle & Reath LLP

(57) ABSTRACT

A scar subcision devices comprising a first elongated element comprising a pivotal connection to a second elongated element, the first elongated element having a blunt distal end, the second elongated element having a proximal-facing cutting edge at a distal end thereof, the device having a first state wherein the cutting edge is retracted to a location within an outer perimeter of the first elongated element, and a second state wherein the cutting edge is exposed outside of the outer perimeter of the first elongated element and the device transitioning between the first state and the second state by the first elongated element and the second elongated element rotating relative to each other about the pivotal connection are disclosed. Methods are also disclosed.

8 Claims, 10 Drawing Sheets

Related U.S. Application Data

(60) Provisional application No. 62/203,010, filed on Aug. 10, 2015.

(51) Int. Cl.
*A61B 17/00* (2006.01)
*A61B 17/32* (2006.01)

(52) U.S. Cl.
CPC .............. *A61B 2017/00761* (2013.01); *A61B 2017/00792* (2013.01); *A61B 2017/00969* (2013.01); *A61B 2017/320044* (2013.01)

(58) Field of Classification Search
CPC ......... A61B 2017/320044; A61B 2017/00761; A61B 17/29; A61B 17/32; A61B 17/28; A61B 17/2812; A61B 17/2816; A61B 10/02; A61B 17/295; A61B 2017/00747
See application file for complete search history.

(56) References Cited

U.S. PATENT DOCUMENTS

| | | | |
|---|---|---|---|
| 5,649,947 A | 7/1997 | Auerbach | |
| 5,728,112 A | 3/1998 | Yoon | |
| 5,749,147 A | 5/1998 | Hasegawa | |
| 5,833,703 A | 11/1998 | Manushakian | |
| 5,988,168 A | 11/1999 | Bair | |
| 7,442,192 B2 | 10/2008 | Knowlton | |
| 7,871,423 B2 | 1/2011 | Livneh | |
| 8,652,123 B2 | 2/2014 | Gurtner | |
| 8,979,881 B2 | 3/2015 | Clark, III | |
| 9,656,399 B2 | 5/2017 | Brainard | |
| 10,117,892 B2 | 11/2018 | Perry | |
| 10,271,866 B2 | 4/2019 | Clark, III | |
| 2003/0130628 A1* | 7/2003 | Duffy | A61B 17/22 604/289 |
| 2003/0158566 A1* | 8/2003 | Brett | A61B 17/3417 606/167 |
| 2006/0172255 A1 | 8/2006 | Hochman | |
| 2006/0241663 A1 | 10/2006 | Rice | |
| 2011/0295297 A1 | 12/2011 | Shirley | |
| 2012/0150208 A1* | 6/2012 | Messmer | A61B 17/320016 606/167 |
| 2013/0090681 A1 | 4/2013 | Young | |
| 2018/0214169 A1 | 8/2018 | Gutwein | |

FOREIGN PATENT DOCUMENTS

| | | |
|---|---|---|
| CN | 202821527 | 3/2013 |
| CN | 204191319 | 3/2015 |
| CN | 104644244 | 5/2015 |
| CN | 204500879 | 7/2015 |
| EP | 2504047 | 10/2012 |
| GB | 2350080 | 11/2000 |

OTHER PUBLICATIONS

International Preliminary Report on Patentability issued by the International Searching Authority, dated Feb. 22, 2018, for International Patent Application No. PCT/US2016/046345; 8 pages.

* cited by examiner

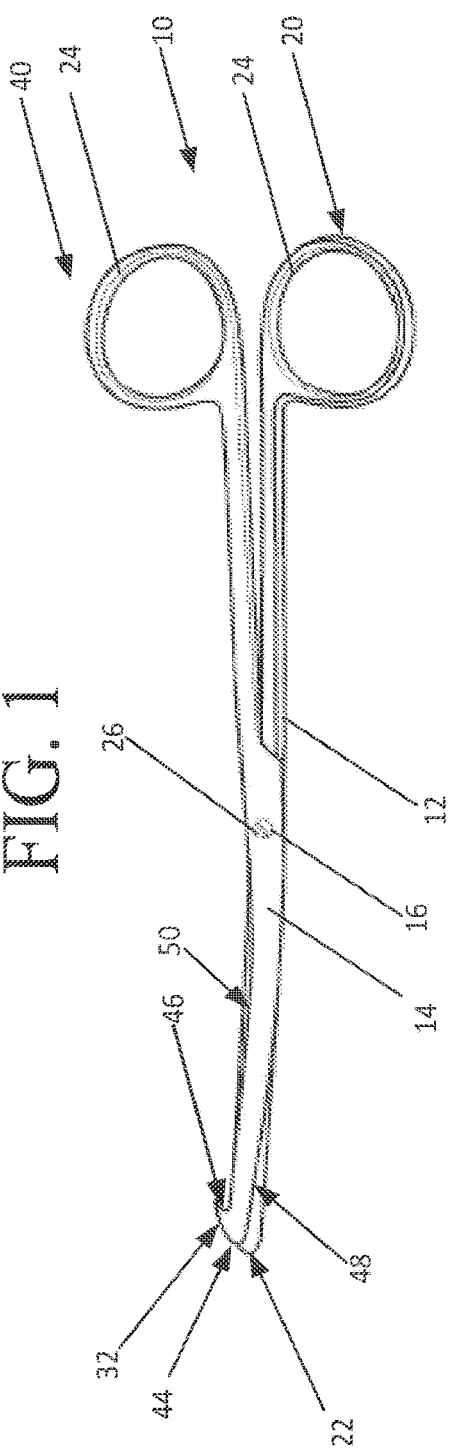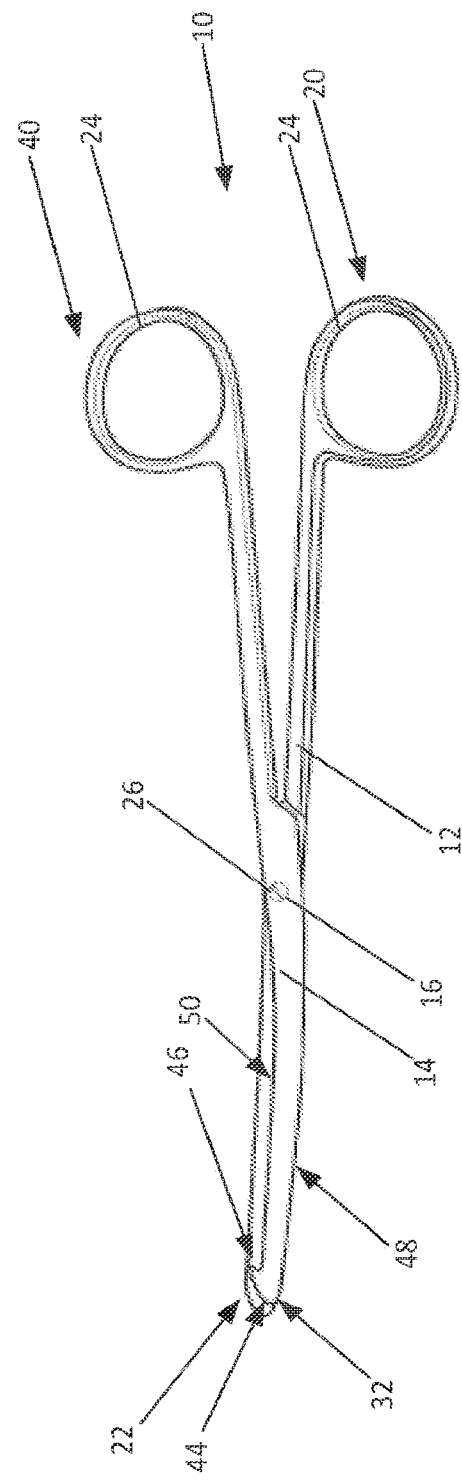

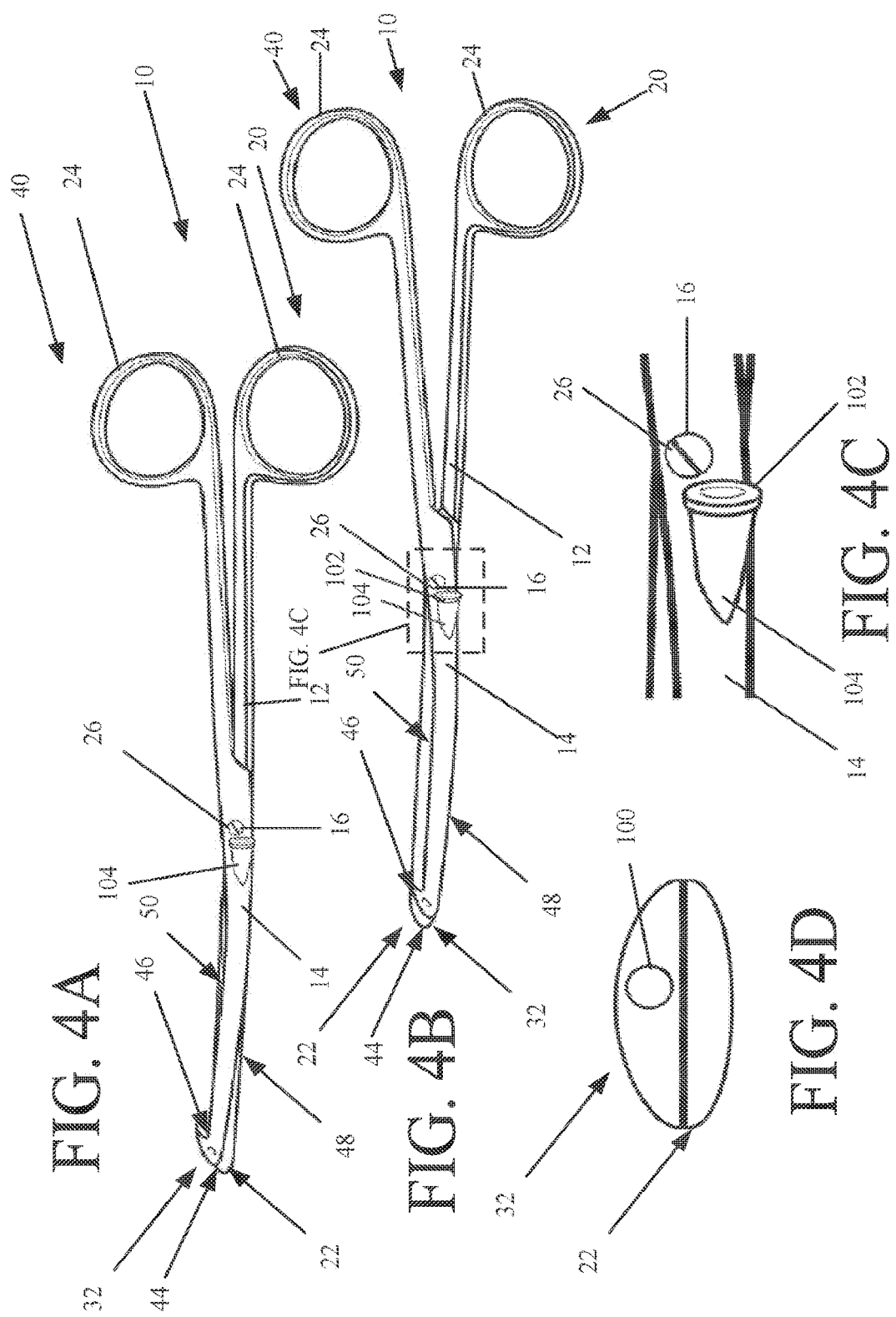

DEVICE AND METHOD FOR SCAR SUBCISION

CROSS-REFERENCE TO RELATED APPLICATIONS

The present application is a continuation of U.S. patent application Ser. No. 15/745,955, filed Jan. 18, 2018, which is a National Phase Application of International Patent Application No. PCT/US2016/46345, filed Aug. 10, 2016, which in turn claims priority to U.S. Provisional Application Ser. No. 62/203,010, filed on Aug. 10, 2015, the entire disclosures of which are hereby expressly incorporated by reference.

FIELD OF THE DISCLOSURE

The present disclosure is related to methods and devices that provide for tissue dissection. The disclosure is more particularly directed to methods and devices that provide for sub-dermal dissection of scar tissue.

BACKGROUND

Subcision is a surgical technique used to manage acne scars, depressed scars, wrinkles, striae, and cellulite. Subcision aims to sever the fibrous attachments beneath the scar at the subdermal level to lift up the scar and induce the formation of connective tissues through normal physiological healing. In the case of acne scars, this is often achieved by using a needle 15 to penetrate the skin and sever fibrous attachments via punctures provided by the needle tip. A needle is introduced into the subdermal space parallel to the skin and moved back and forth as well as in a fanning motion to release the skin.

Larger scars, such as bum scars, can require a larger dissection instrument to efficiently treat the larger area. Bum scars often are formed as part of a skin graft (partial thickness skin graft or split thickness skin graft). Bum scars (including hose that involved a skin graft) benefit from additional treatment in the form of lipotransfer and transfer of adipocytes.

In order to transfer adipocytes beneath a skin graft, a space must be created between the graft and the underlying fascia/muscle. The conventional method for achieving this space begins by making a stab incision or an approximately 3 mm entry point adjacent to the graft circumference with a scalpel or needle. Next, a conventional instrument available such as a hemostat or mosquito clamp is introduced through the stab incision to bluntly create the space for adipocyte deposition. Design of the conventional instruments limit efficiency and safety of the scar subcision process because of the limited length necessitating multiple entry points and the lack of a sharp blade for sharp scar incision. By creating the space exclusively with blunt dissection, unnecessary tissue injury occurs which may lead to an open wound.

SUMMARY

In a first aspect of the present disclosure, there is provided a scar subcision device including: first and second elongated elements coupled via a hinge; the first elongated element having a blunt distal end; the second elongated element having a blade at a distal end thereof; the device having a first state where the blade is retracted to a location within an outer perimeter of the first elongated element; the device having a second state where the blade is exposed outside of the outer perimeter of the first elongated element; the device transitioning between the first and second states by the first and second elongated elements rotating relative to each other about the hinge. In some aspects, the blade is disposed on a proximal facing surface of the second 15 elongated element. In some aspects, the first elongated element includes a passageway defined therein having an inlet in a proximal end of the first elongated element and an outlet at the distal end of the first elongated element. The device may include a luer lock coupled to the inlet of the passageway. The device may include finger loops at proximal ends of each of the first and second elongated elements.

In a second aspect of the present disclosure, there is provided a scar subcision device comprising: a first elongated element pivotally connected by a pivot to a second elongated element; the first elongated element having a blunt distal end; the second elongated element having a proximal-facing cutting edge at a distal end thereof; the device having a first state where the cutting edge is retracted to a location within an outer perimeter of the first elongated element; the device having a second sate where the proximal-facing cutting edge is exposed outside of the outer perimeter of the first elongated element; the device transitioning between the first state and the second state by the first elongated element and second elongated element rotating relative to each other about the pivot. In some aspects, the device further comprises a biasing member configured to bias the scar subcision device in the first state. In some aspects, at least one of the first elongated element, the second elongated element, or both comprise an orifice extending from a proximal portion of the scar subcision device to the distal end. The proximal portion may be the proximal end of the scar subcision device. The first elongated element may comprise the orifice. The orifice may be a bore or a groove. In some aspects, the device comprises a transitioning governor configured to limit rotation of the first element, the second element, or both. The transitioning governor may comprise a slot and a pin. The biasing member may be a spring. The spring may be a spring wire. The first elongated element, the second element, or both may comprise a handle. The handle may be a handle ring. The device may comprise a finger hook.

In a third aspect of the present invention, there is provided a method for creating a space beneath a skin graft comprising: making a stab incision, inserting a scar subcision device comprising a first elongated element pivotally connected by a pivot to a second elongated element, the first elongated element having a blunt distal end, the second elongated element having a proximal-facing cutting edge at a distal end thereof, the device having a first state where the cutting edge is retracted to a location within an outer perimeter of the first elongated element, the device having a cutting state where the proximal-facing cutting edge is exposed outside of the outer perimeter of the first elongated element, and the device transitioning between the first and cutting states by the first elongated element and second elongated element rotating relative to each other about the pivot; deploying the scar subcision device in the cutting state; and dissecting a graft from an underlying fascia.

It will be appreciated that numerous modifications to the abovementioned aspects of the present disclosure may be made without departing from the scope of the disclosure as defined in the appended claims. Moreover, any one or more of the above described aspects could be combined with one or more of the other aspects to suit a particular application.

Optional and/or preferred features may be used in other combinations beyond those described herein, and optional and/or preferred features described in relation to one aspect of the present disclosure may also be present in another aspect or aspect of the present disclosure, where appropriate.

The described and illustrated aspects are to be considered as illustrative and not restrictive in character, it being understood that only the preferred aspects have been shown and described and that all changes and modifications that come within the scope of the disclosure(s) as defined in the claims are desired to be protected. It should be understood that while the use of words such as "preferable", "preferably", "preferred" or "more preferred" in the description may suggest that a feature so described may be desirable, it may nevertheless not be necessary and aspects lacking such a feature may be contemplated as within the scope of the present disclosure as defined in the appended claims. In relation to the claims, it is intended that when words such as "a," "an," or "at least one," are used to preface a feature there is no intention to limit the claim to only one such feature unless specifically stated to the contrary in the claim.

BRIEF DESCRIPTION OF THE DRAWINGS

The above-mentioned aspects of the present teachings and the manner of obtaining them will become more apparent and the teachings will be better understood by reference to the following description of the aspects taken in conjunction with the accompanying drawings, wherein:

FIG. 1 is a plan view of a dissection device of a first aspect of the present disclosure in an open orientation;

FIG. 2 is a plan view of the device of the first aspect of the present disclosure in a closed orientation;

FIGS. 4A-D show a dissection device according to a second aspect of the present disclosure;

DETAILED DESCRIPTION

The various aspects of this disclosure are not intended to be exhaustive or limit the invention to the precise forms disclosed in the following detailed description. Rather, the aspects were chosen and described so that others skilled in the art may utilize their teachings.

Figure 3A:
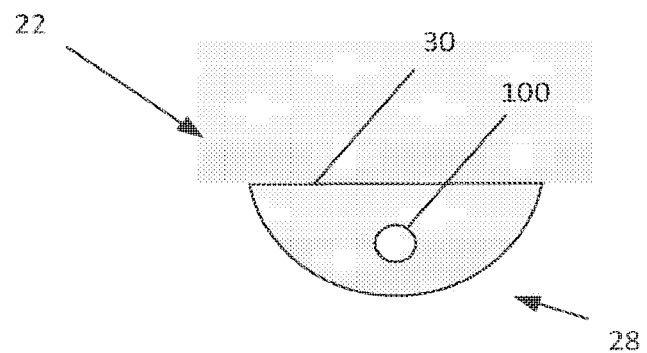
FIGS. 3A and 3B are exemplary end views of one tine of the device of FIGS. 1 and 2.
Figure 3B:
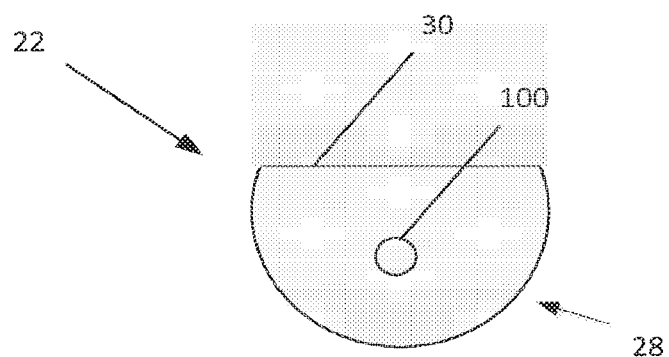

An exemplary aspect of the present disclosure is shown in FIGS. 1 and 2. Subcision device 10 includes blunt tine 12, cutting tine 14, and fulcrum screw or hinge 26. Blunt tine 12 includes a proximal end 20, and a distal end 22. Proximal end 20 includes a finger receiver 24 that is similar to that found on scissors or hemostats. Fulcrum hole 16 is provided between proximal end 20 and distal end 22 and . Distal end 22 is a rounded blunt end. Distal end 22 is rounded in the direction that is "up-and-down" in FIG. 1 and is also rounded in the direction into the page of FIG. 1 such that the distal end presents a rounded blunt leading end without sharp edges. FIGS. 3A and 3B show exemplary contours of distal end 22. Lower side 28 is rounded. Upper side 30 is flat and provides a surface for engaging a distal end 32 of cutting tine 14 (shown in FIGS. 1 and 2). In certain aspects, blunt tine 12 (FIGS. 1 and 2) includes an internal passageway 100 that extends therein from near proximal end 20 to near distal end 22. Other aspects (FIGS. 4A-4D) provide passageway 100 in cutting tine 14. Passageway 100 is open to ambient at the proximal and distal ends thereof. In one aspect, FIGS. 4A-D a luer lock 102 (and potentially an amount of tubing 104) is coupled to passageway 100 at the proximal end thereof.

Referring again to FIGS. 1 and 2, cutting tine 14 includes proximal end 40 and distal end 32. Proximal end 40 is similar to proximal end 20 and provides finger receiver 24. Another fulcrum hole 16 is provided between proximal end 40 and distal end 32. Distal end 32 includes a rounded tip 44 and rear-facing cutting edge 46. Rounded tip 44 provides a blunt distal edge. Cutting edge 46 provides a hook with a sharpened proximal-facing surface. Cutting tine 14 also includes first and second lateral sides 48, 50. In certain aspects, first and second lateral sides 48, 50 include sharpened cutting surfaces as well. However, the pictured aspect does not have sharp first and second lateral sides 48, 50.

Blunt tine 12 and cutting tine 14 are linked via fulcrum screw or hinge 26. Subcision device 10 thus operates such that tines 12, 14 hinge relative to each other about fulcrum screw or hinge 26 to have motion often associated with scissors and hemostats.

Aspects of subcision device IO are envisioned where one of blunt tine 12 and cutting tine 14 includes a stabilizer (not shown) that extends from proximal end 20 or 40 in the direction of the proximal end 40 or 20 of the other tine. One such example is the lock extensions of hemostats. Another such example is a flexible member that holds apart the proximal ends 20, 40 with a force that can be overcome by a human hand when desired. Aspects are further envisioned with a number of diameters and lengths of proximal ends 20, 40 and distal ends 22, 32 as well as a number of contours (curves or otherwise) of the ends 20, 22, 40, 32. Furthermore, aspects are envisioned where the size (diameter, cross-sectional area) of tines 12, 14 tapers from their proximal ends to their distal ends.

In use, a medical professional makes an access incision proximate a scar area to be treated. Once access is obtained, subcision device 10 is obtained in a state (e.g., a closed orientation) where distal ends 22, 32 of tines 12, 14 overlap such that any cutting edge (such as cutting edge 46) does not extend laterally of the lateral edges of blunt tine 12. Blunt edge is then used to forcibly create a space between the skin (which is potentially the product of a skin graft) and the underlying tissue. The blunt end of blunt tine 12 provides a reduced likelihood of inadvertently causing the subcision device to pierce through the skin or to make any undesired perforation of anatomy. The desired effect is providing separation between the skin and the underlying tissue to create a void there-between. In certain places, scar tissue will be tougher than others such that a blunt surface is urged elsewhere as it is urged forward by a user. This redirection of subcision device 14 by the anatomy provides an element of unpredictability in the placement of distal end 22, 32. This is another reason that presenting a blunt distal end is desired in that travel of the distal ends 22, 32 is sometimes at least partially controlled by the tissue rather than a user's desire. With subcision device 10 so located, subcision device 10 is often moved laterally (hinging at the entry point) or is retracted to prepare to make another path.

If at any point, anatomy is encountered (such as especially thick scar tissue), a user can push device IO to the side of and past that scar tissue. The user then urges proximal ends 20, 40 together to cause relative rotation at distal ends 22, 32 and to expose cutting edge 46 (e.g., placing the scar subcision device in the open orientation). The user then retracts device 10 to cause the exposed cutting edge 46 to encounter the scar tissue. Further retraction causes the scar tissue to be cut by cutting edge 46. It should be appreciated that the retraction of device 10 is a more controlled operation than the forward movement plunging into anatomy. Retraction pulls device 10 back towards the incision entry point. Furthermore, upon retraction, the path of device 10 is more known. Thus, during retraction there is a reduced risk of encountering undesired tissue relative to the forward movement of device 10. In this manner, cutting edge 46 is able to be located at scar tissue to allow additional release of skin from underlying tissue. Once the scar tissue is cut, cutting edge 46 is retracted by urging proximal ends 20, 40 apart to cause relative rotation at distal ends 22, 32 and to "hide" cutting edge 46.

Once the desired gaps are created between skin and the underlying tissue, lipotransfer and transfer of adipocytes can take place. A syringe containing fat and adipocytes is attached (via luer lock 102 and tubing 104 or otherwise) to provide those fats and adipocytes to passageway 100. The syringe is thus able to urge fat and adipocytes through passageway 100 and out into the patient at the distal end of passageway 100 proximate the distal end of blunt tine. A syringe plunger is depressed as device 10 is retracted to deposit a line of fat and adipocytes out of the distal end of the passageway 100.

Additional aspects are envisioned where the distal cutting edge 46 is exposed by other than the scissor-like action of blunt tine 12 and cutting tine 14. Such aspects include but are not limited to cable actuated movement and pneumatic actuated movement. It should be appreciated that the provided example provides a neutral resting position in which no cutting surface is exposed. Stated differently, when device 10 does not have a user-provided force acting thereupon, no cutting surface is exposed. In some aspects, device 10 is biased to a position that retracts any and all cutting surfaces such that in the absence of force acting thereupon, device 10 self-conceals any cutting surfaces.

Figure 5A:
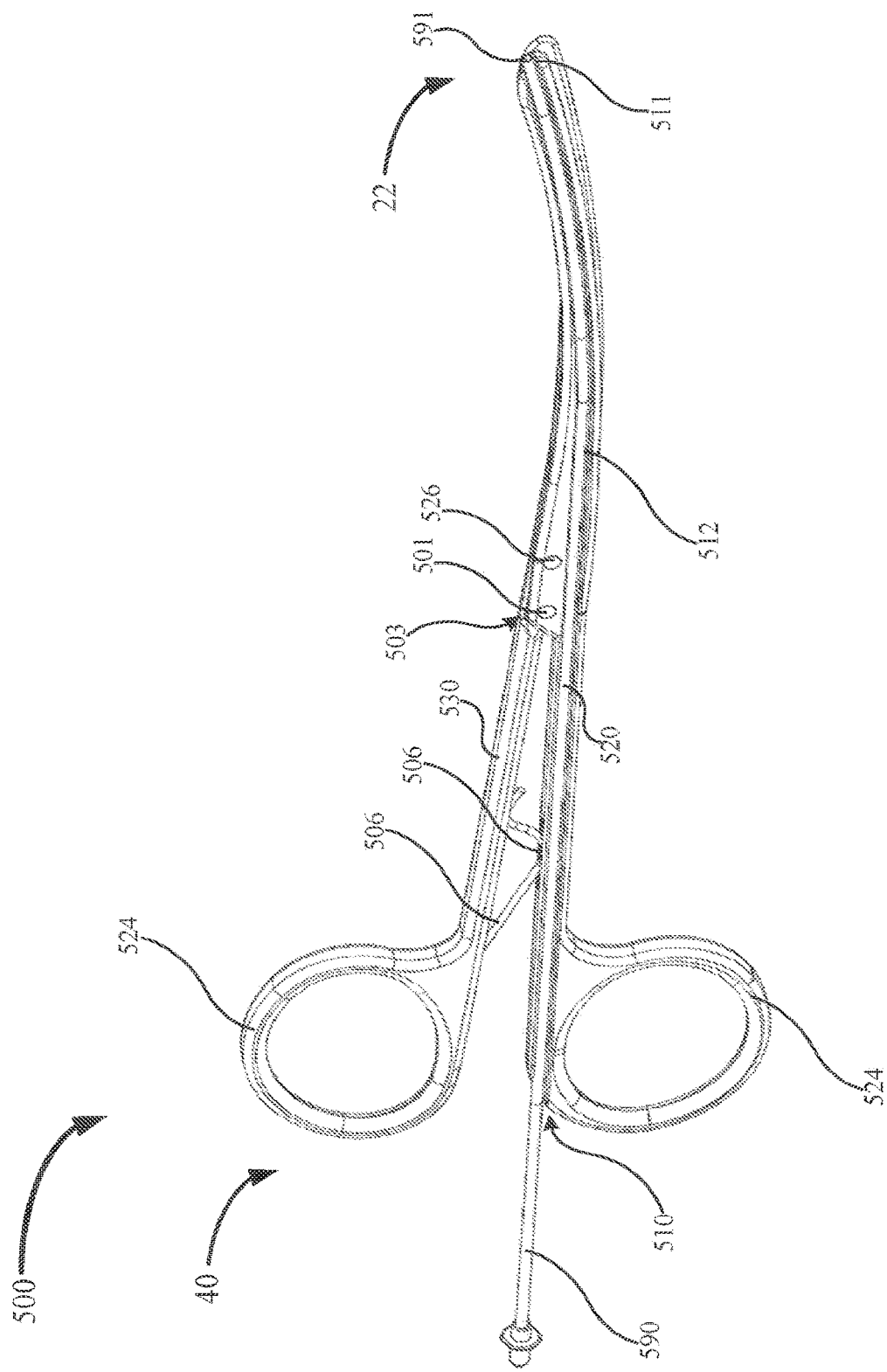
FIGS. 5A-C are perspective views of a scar subcision device having a groove according to various aspects of the present disclosure.
Figure 5B:
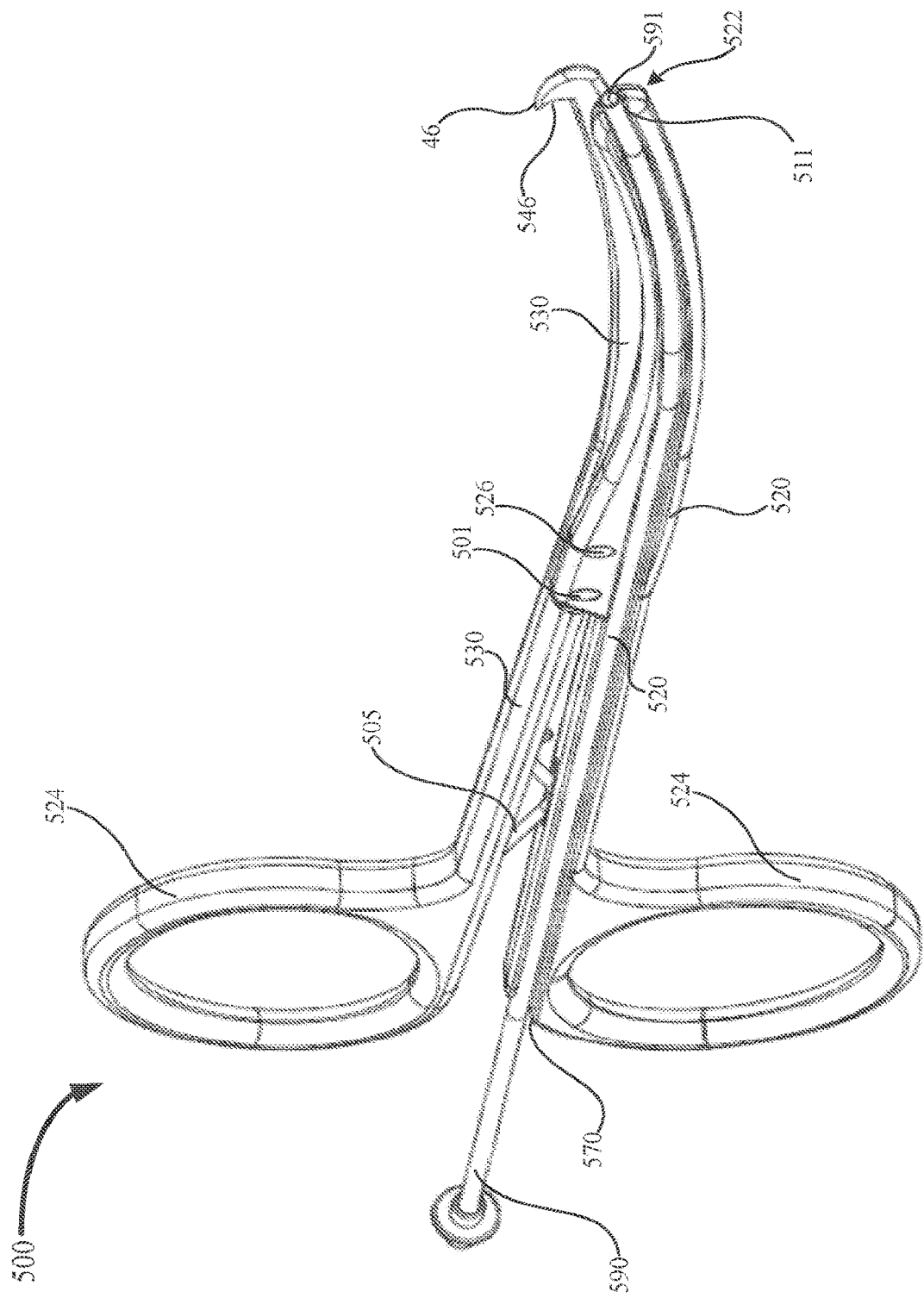
Figure 5C:
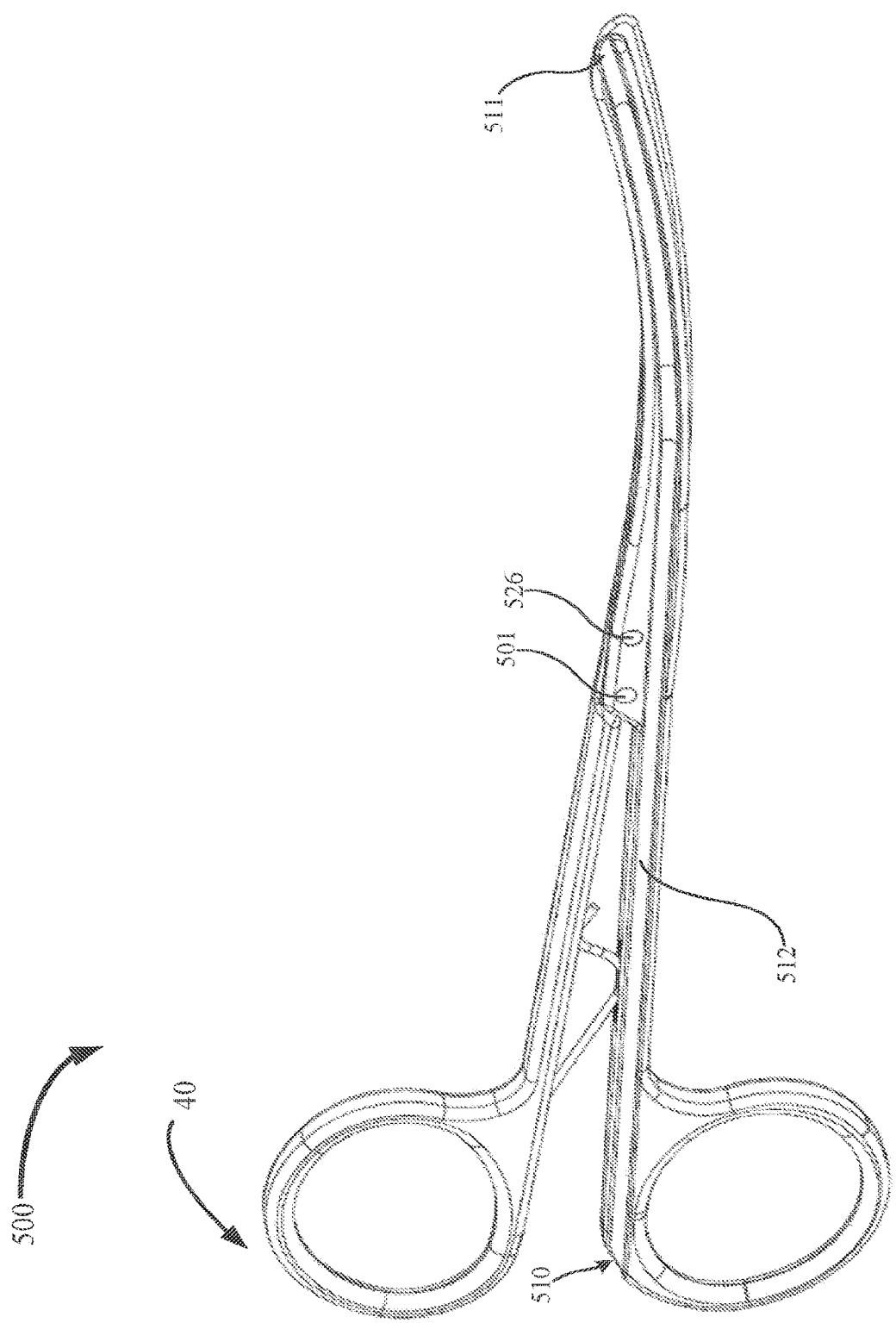

FIGS. 5A-5C provide various perspective views of a scar subcision device 500 according to various aspects of the disclosure. Scar subcision device 500 may including a first elongated element 520 pivotally connected by a pivot 526 to a second elongated element 530, the first elongated element 520 may have a blunt distal end 522 (FIG. 5B). The second elongated element 530 includes a proximal-facing cutting edge 546 (FIG. 5B) at distal end 22. In various aspects, scar subcision device 500 may include a first, closed state (shown in FIGS. 5A and 5C) where the proximal-facing cutting edge 546 may be retracted to a location within an outer perimeter of the first elongated element 520. In various aspects, scar subcision device 500 may have a second state (illustrated in FIG. 5B) where the proximal-facing cutting edge 546 is exposed outside of the outer perimeter of the first elongated element 520. Thus, in various aspects, scar subcision device may be configured to transition between the first state (shown in FIGS 5A and 5C) and the second, open state (shown in FIG. 5B) by the first elongated element 520 and second elongated element 530 rotating relative to each other about the pivot 526.

In various aspects, scar subcision device 500 may comprise a biasing member configured to bias the scar subcision device 500 in the first state. For example, FIGS. 5A-C shows an aspect where the biasing member is a spring, such as a spring wire 505, which may be secured in wire aperture 506. In some aspects, the first elongated element 520, the second element 530, or both comprise a handle, such as handle ring 524. Also, in some aspects, one or more handles may comprise a finger ring.

In some aspects, the transitioning governor of the scar subcision device 500 may comprise a transitioning governor configured to limit the rotation of the first elongated element 520, the second elongated element 530, or both. In some aspects, the scar subcision device 500 may comprise a slot 503 and a pin 501, such as that shown in FIG. 5A. In various aspects, the pin 501 may limit the rotation of the first elongated element 520 and the second elongated element 530 to a predetermined distance, which may limit or govern the travel of the distal end 22 of the scar subcision device 500.

In various aspects, the scar subcision device 500 and scar subcision device 600 (shown in FIGS. 6A-C) may comprise an orifice extending from a proximal portion of the scar subcision device to a distal end. For example, at least one of the first elongated element 520, the second elongated element 530, or both may comprise an orifice extending from a proximal portion of the scar subcision device to a distal end 22. In various embodiments, the proximal portion may be the proximal end 40 of the scar subcision device.

In various aspects, the orifice extends along the length of the elongated element, such as the first elongated element 520. In some aspects, the orifice may be a groove, such as groove 512 shown in FIGS. 5A-5C. With reference to FIG. 5C, scar subcision device 500 is shown with syringe 590 removed. In some instances, aspects having a groove, such as groove 512 may be desirable to facilitate the cleaning of the scar subcision device. In some aspects, the syringe may be retained within groove 512, or may be inserted in proximal end 510 and pushed down groove 512 to distal end 511.

Figure 6A:
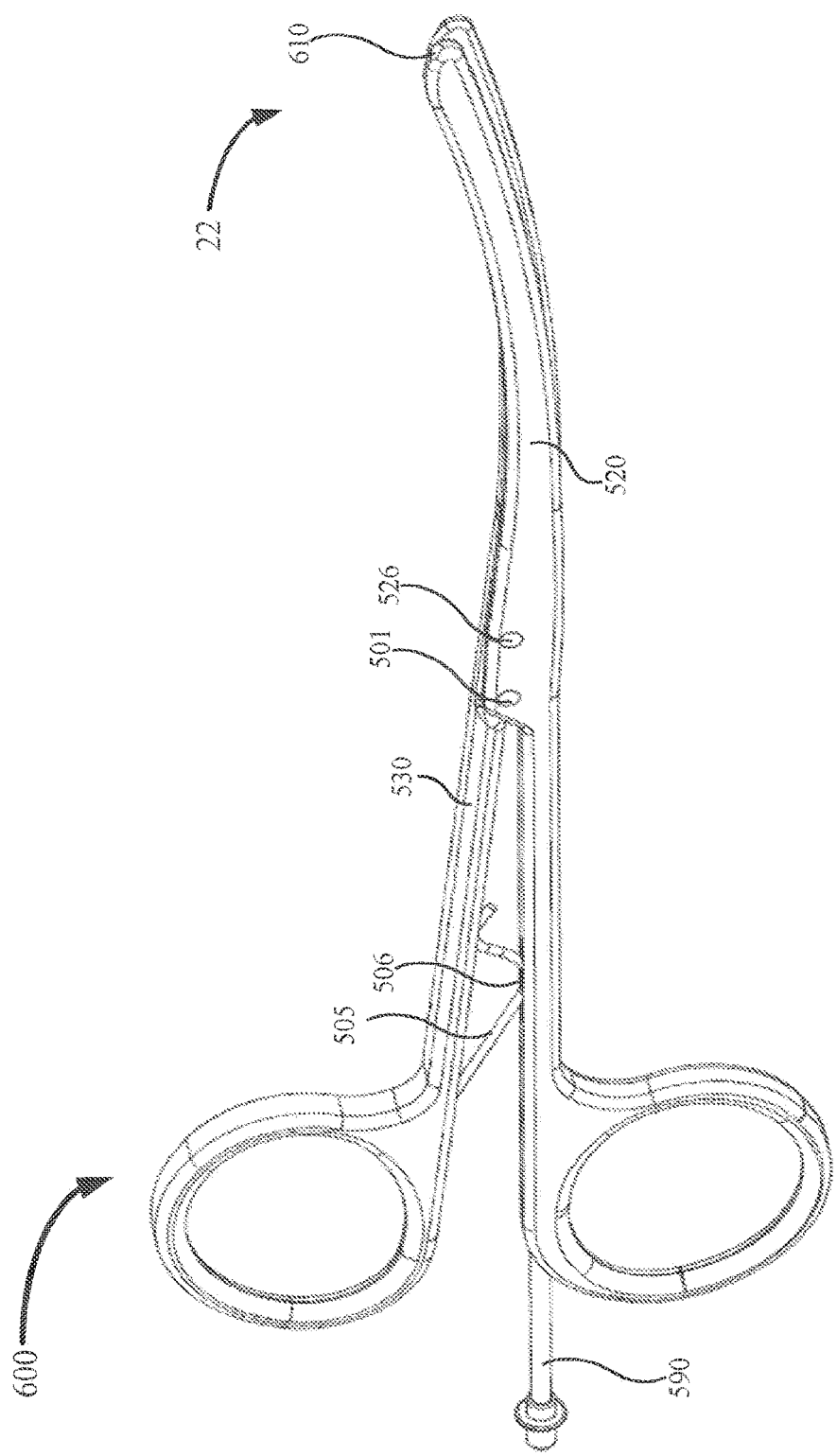
FIGS. 6A-C are various perspective views of a scar subcision device according to various aspects of the present disclosure.
Figure 6B:
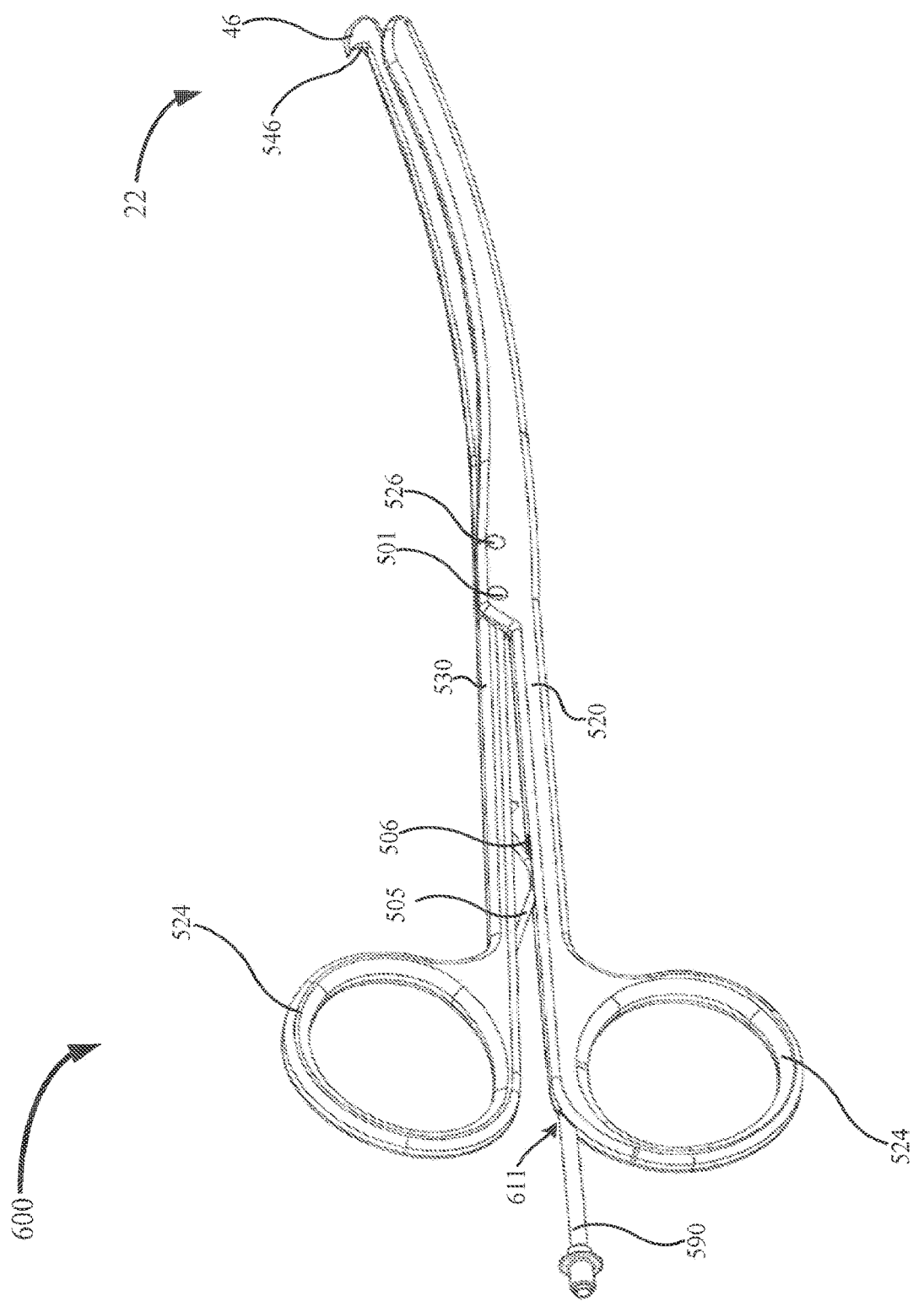
Figure 6C:
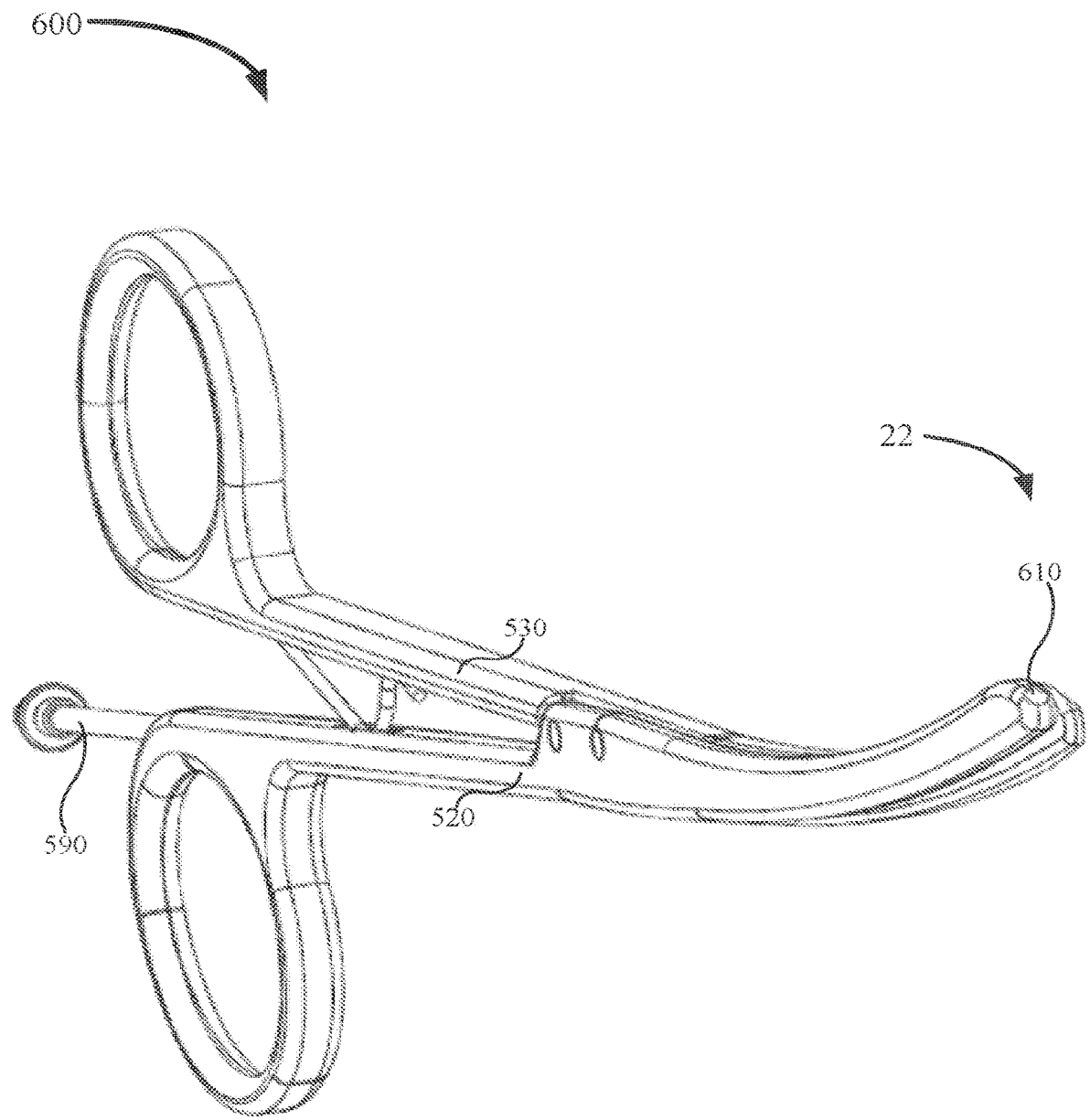

In some aspects, the orifice may be a bore, such as bore 610 (shown in FIGS. 6A, and 6C). In various aspects, the orifice may be configured to receive a syringe, such as syringe 590. In various aspects, syringe 590 may be inserted into bore 610 at a proximal opening 611 and pushed in a distal direction towards distal end 22.

Figure 7:
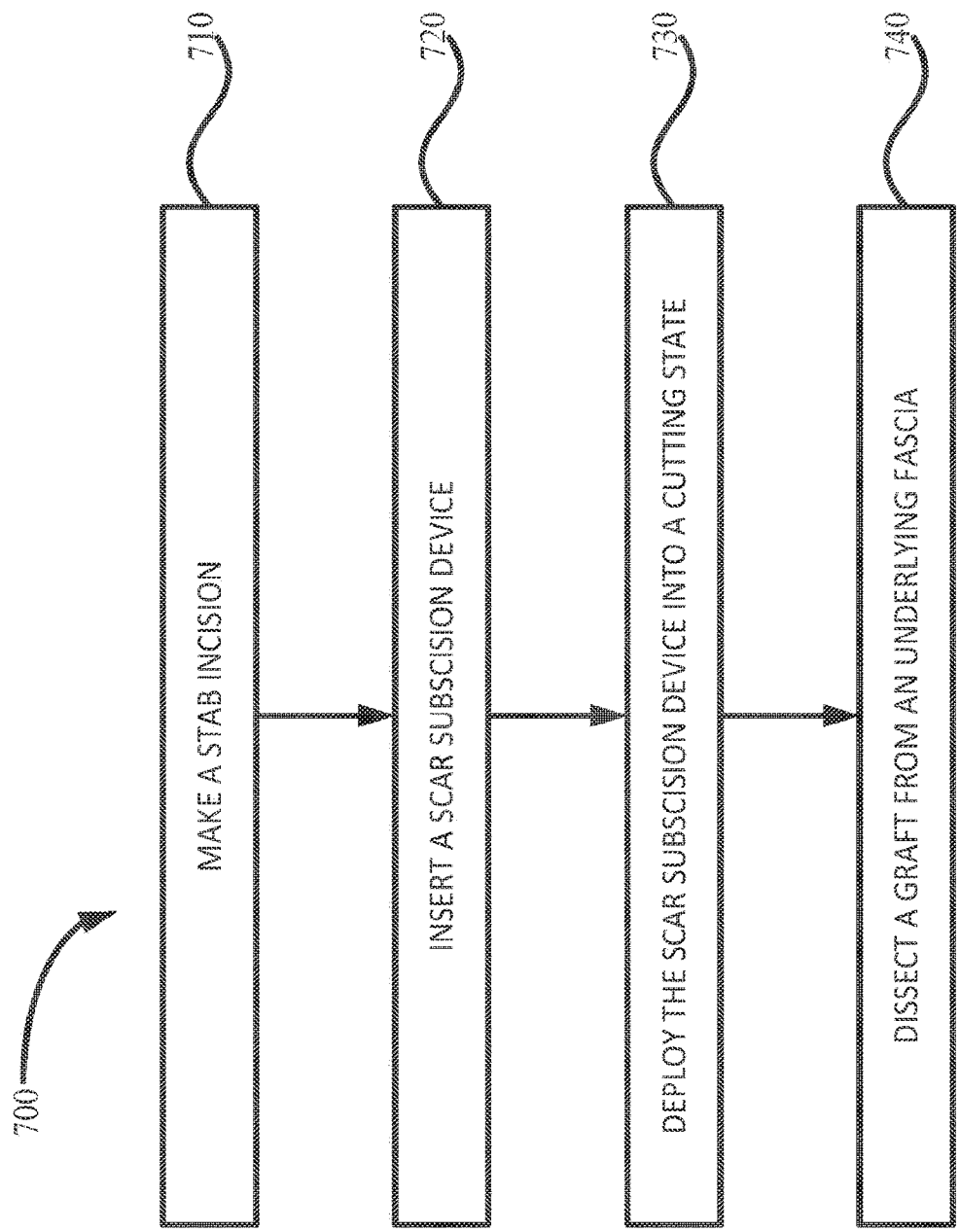
FIG. 7 is a block diagram of a method according to various aspects of the present disclosure.

FIG. 7 is a flow diagram showing methods for creating a space beneath a skin graft. Method 700 may comprise making a stab incision (step 710), inserting a scar subcision device (step 720) into the stab incision, deploying the scar subcision device in the cutting state (step 730), and dissecting a graft from an underlying fascia (step 740).

In various aspects, the scar subcision device in method 700 may include any scar subcision device disclosed herein. For example, scar subcision device may comprise a first elongated element pivotally connected by a pivot to a second elongated element, the first elongated element having a blunt distal end, the second elongated element having a proximal facing cutting edge a distal end thereof, the device having a first state where the blade is retracted to a location within an outer perimeter of the first elongated element, the device having a cutting state where the proximal-facing cutting edge is exposed outside of the outer perimeter of the first elongated element, and the device transitioning between the first and cutting states by the first and second elongated elements rotating relative to each other about the pivot.

The above detailed description and the examples described therein have been presented for the purposes of illustration and description only and not for limitation. For example, the operations described may be done in any suitable manner. The method may be done in any suitable order still providing the described operation and results. It is therefore contemplated that the present aspects cover any and all modifications, variations or equivalents that fall within the spirit and scope of the basic underlying principles disclosed above and claimed herein.

The invention claimed is:

1. A method of subcision comprising:

making an access incision in skin;

inserting a subcision device having a rounded blunt leading end into the access incision, the device comprising a first element comprising a pivotal connection to a cutting element, the first element having a blunt surface, the cutting element having a hook with a rear-facing cutting edge forming an acute angle, the device having a closed state wherein the cutting edge is retracted to a location substantially within an outer perimeter of the device, and a cutting state where the rear-facing cutting edge is exposed outside of the outer perimeter of the device;

pushing the subcision device in the closed state to a position wherein the rear-facing cutting edge is past tissue to be cut;

transitioning the subcision device to the cutting state by the first element and the cutting element rotating relative to each other about the pivotal connection in a scissor-like action;

retracting the subcision device to cause the exposed rear-facing cutting edge to encounter the tissue to be cut; and further retracting the subcision device to cause the tissue to be cut by the rear-facing cutting edge.

2. The method of claim 1, further comprising:

rotating the first element and cutting element relative to each other to return to the closed state.

3. The method of claim 1, further comprising:

pushing the subcision device in the closed state to a position wherein the rear-facing cutting edge is to the side of tissue to be cut.

4. The method of claim 3, further comprising:

rotating the first element and cutting element relative to each other to return to the closed state.

5. The method of claim 1, wherein the tissue is fibrous attachments causing an acne scar.

6. The method of claim 1, wherein the tissue is fibrous attachments causing a depressed scar.

7. The method of claim 1, wherein the tissue is fibrous attachments causing cellulite.

8. The method of claim 1, further comprising injecting fat into a location where the tissue has been cut.

* * * * *